US010330497B1

(12) United States Patent
Moore et al.

(10) Patent No.: US 10,330,497 B1
(45) Date of Patent: *Jun. 25, 2019

(54) MODIFIED EDDY CURRENT PROBE HAVING A FARADAY SHIELD

(71) Applicant: Centrus Energy Corp., Bethesda, MD (US)

(72) Inventors: James A. Moore, Bethesda, MD (US); Michael S. Emery, Powell, TN (US); Marc L. Simpson, Knoxville, TN (US); Mike Hileman, Bethesda, MD (US); Terry White, Bethesda, MD (US)

(73) Assignee: Centrus Energy Corp., Bethesda, MD (US)

( * ) Notice: Subject to any disclaimer, the term of this patent is extended or adjusted under 35 U.S.C. 154(b) by 226 days.

This patent is subject to a terminal disclaimer.

(21) Appl. No.: 15/430,601

(22) Filed: Feb. 13, 2017

(51) Int. Cl.
 *G01D 5/20* (2006.01)
 *H05K 1/18* (2006.01)
 *H01F 27/28* (2006.01)

(52) U.S. Cl.
 CPC ....... *G01D 5/2006* (2013.01); *H01F 27/2804* (2013.01); *H01F 27/2885* (2013.01); *H05K 1/18* (2013.01); *H01F 2027/2809* (2013.01)

(58) Field of Classification Search
 None
 See application file for complete search history.

(56) References Cited

U.S. PATENT DOCUMENTS

| 5,021,738 A * | 6/1991 | Vernon | G01N 27/9033 324/232 |
| 5,059,904 A * | 10/1991 | Mazzone | G01N 27/902 324/219 |
| 6,636,037 B1 * | 10/2003 | Ou-Yang | G01N 27/902 324/232 |
| 10,041,812 B1 * | 8/2018 | Simpson | G01D 5/2006 |
| 2014/0167745 A1 * | 6/2014 | Held | G01B 21/045 324/207.12 |

OTHER PUBLICATIONS

Roach, "Designing and Building an Eddy Current Position Sensor", Sensors Magazine, Sep. 1998, pp. 1-17.

* cited by examiner

Primary Examiner — Paresh H Patel
(74) Attorney, Agent, or Firm — MacMillan, Sobanski & Todd, LLC (57) ABSTRACT

A modified eddy current (MEC) probe includes a probe body having a bore formed therein. A printed circuit board (PCB) assembly includes a circuit board defining a plane, has a plurality of electronic components mounted thereon, and is configured for mounting within the bore of the probe body. A coil board assembly is electrically connected to the PCB assembly, defines a plane, and includes a first coil board layer, a second coil board layer bonded to the first coil board layer, a transmitter coil formed on an outside surface of the first coil board layer, a Faraday shield formed on an outside surface of the second coil board layer, and a sensor coil formed on one of an inside surface of the first coil board layer and the second coil board layer, such that the sensor coil is positioned between the first coil board layer and the second coil board layer. The plane of the coil board assembly is arranged orthogonally to the plane of the circuit board.

20 Claims, 7 Drawing Sheets

MODIFIED EDDY CURRENT PROBE HAVING A FARADAY SHIELD

GOVERNMENT LICENSE RIGHTS

This invention was made with government support under contract numbers ORNL00-0579 and 4000130255 awarded by Oak Ridge National Laboratory. The government has certain rights in the invention.

BACKGROUND OF THE INVENTION

This invention relates to an eddy current probe configured to accurately measure a distance between the eddy current probe and a surface of an object spaced apart from the eddy current probe. In particular, this invention relates to an improved or modified eddy current probe (MEC) that may be used in groups of two or more to measure the distance to multiple locations on a surface of an object, including objects formed from a low conductivity material, and are configured to operate without undesirable noise and cross-talk caused by coupling of the electro-magnetic fields of closely spaced eddy current probes.

Known eddy current probes are configured to monitor and analyze rotating and reciprocating machinery and measure the distance between an eddy current probe and a surface of an object. Typically, an eddy current probe is positioned near a monitored target object such as a rotating shaft of a machine or an outer race of a rolling element bearing. Known eddy current probes are designed to monitor and/or measure the distance to the surface of high conductivity materials such as metals. Further, known eddy current probes operate at frequencies within the range of about 500 KHz to about 1 MHz.

Carbon fiber composite materials, such as graphite are used in a variety of structures, including carbon brushes for motors, seals and bearings, vane pump components, assemblies for fuel pumps, starters, and alternators, and bi-polar plated for fuel cells. Additionally, graphite structures are used in rotating devices wherein higher bandwidths and sub-mil resolution are required. There is therefore a need in many industries to measure the distance to the surfaces of graphite structures and to locate cracks or defects in the surfaces of graphite structures. Industries with such a need include the power, aircraft, automotive, turbine, mass transit, and railway industries.

Known sensor technology, including eddy current sensors, capacitive sensors, magnetic sensors, and acoustic sensors, are not able to measure the distance to low conductivity materials, such as graphite. Further, these known sensors are not able to monitor and analyze, such as for inspection and balancing, rotating components formed from low conductivity materials, such as graphite.

In some applications, there is a need to measure the distance to multiple locations on the surface of the object. In this situation, two or more eddy current probes may be used. However, the signals from adjacent eddy current probes may undesirably couple, resulting in inaccurate distance measurements.

Thus, it would be desirable to provide an improved structure for an eddy current probe that allows two or more of the eddy current probes to be used together to accurately monitor, analyze, and measure the distance between the probes and a surface of an object, including an object formed from a low conductivity material such as graphite, without undesirable noise and cross-talk caused by coupling of the electro-magnetic fields of adjacent eddy current probes.

SUMMARY OF THE INVENTION

This invention relates to an improved or modified eddy current probe (MEC) that can accurately monitor, analyze, and measure the distance between the probe and a surface of an object formed from a low conductivity material such as graphite.

In one embodiment, the MEC probe includes a modified eddy current (MEC) probe includes a probe body having a bore formed therein. A printed circuit board (PCB) assembly includes a circuit board defining a plane, has a plurality of electronic components mounted thereon, and is configured for mounting within the bore of the probe body. A coil board assembly is electrically connected to the PCB assembly, defines a plane, and includes a first coil board layer, a second coil board layer bonded to the first coil board layer, a transmitter coil formed on an outside surface of the first coil board layer, a Faraday shield formed on an outside surface of the second coil board layer, and a sensor coil formed on one of an inside surface of the first coil board layer and the second coil board layer, such that the sensor coil is positioned between the first coil board layer and the second coil board layer. The plane of the coil board assembly is arranged orthogonally to the plane of the circuit board.

In another embodiment, a MEC probe system includes a plurality of MEC probes configured to cooperate with each other. Each MEC probe includes a probe body having a bore formed therein, a PCB assembly including a circuit board defining a plane and having a plurality of electronic components mounted thereon, wherein the PCB assembly is configured for mounting within the bore of the probe body, and a coil board assembly electrically connected to the PCB assembly. The coil board assembly defines a plane and includes a first coil board layer, a second coil board layer bonded to the first coil board layer, a transmitter coil formed on an outside surface of the first coil board layer, a Faraday shield formed on an outside surface of the second coil board layer, and a sensor coil formed on an inside surface of the first coil board layer or the second coil board layer, such that the sensor coil is positioned between the first coil board layer and the second coil board layer. The plane of the coil board assembly is arranged orthogonally to the plane of the circuit board. The Faraday shields are configured to isolate a propagating transverse electro-magnetic (TEM) field emitted by each MEC probe and prevent or reduce coupling of electro-magnetic fields from the transmitter coil to the plurality of electronic components mounted on the PCB assembly.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
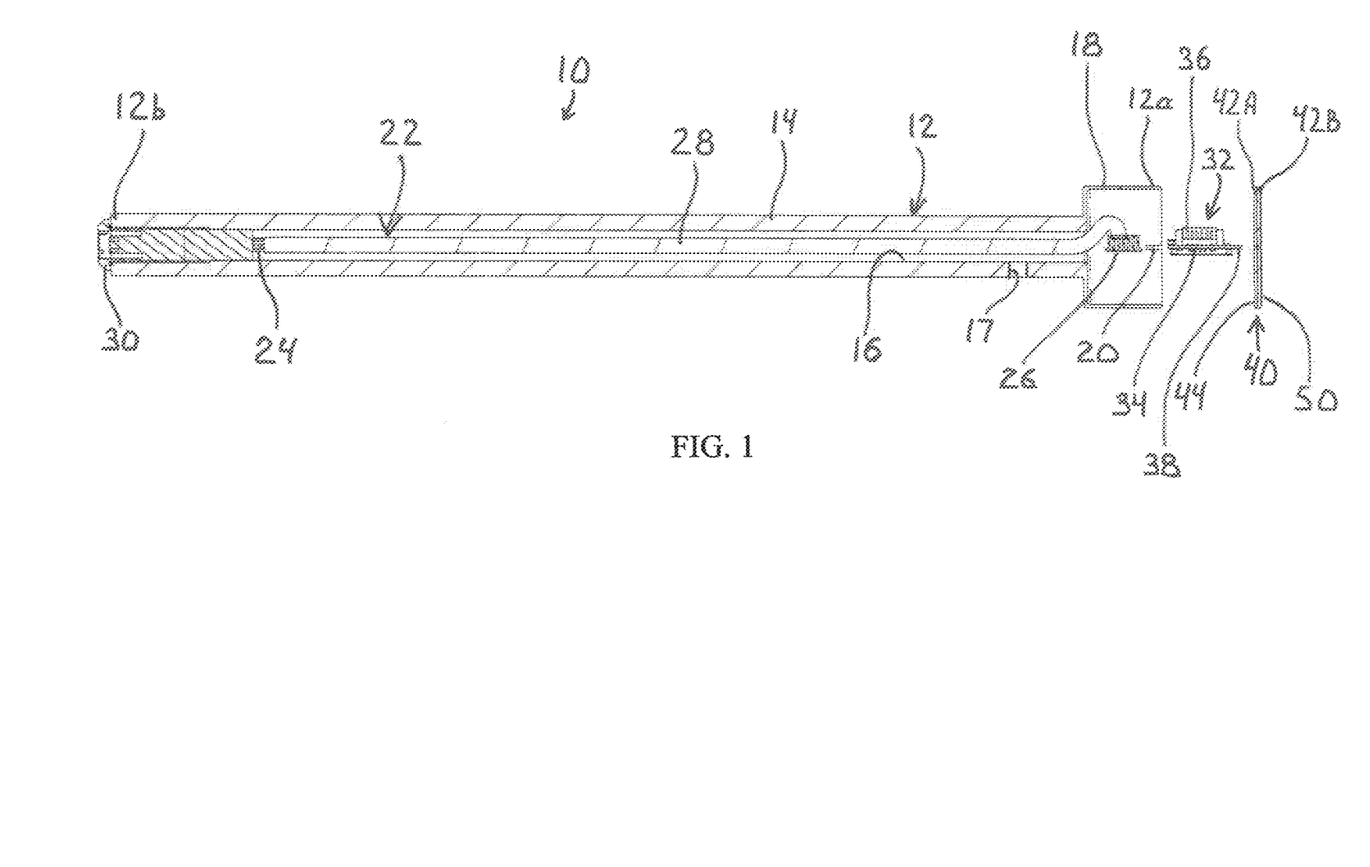
FIG. 1 is a partially exploded cross-sectional view of a modified eddy current (MEC) probe in accordance with this invention.

Referring now to the drawings, there is illustrated in FIG. 1 the structure of an improved or modified eddy current (MEC) probe 10 in accordance with this invention. The MEC probe 10 includes a probe body 12 having a first end 12a and a second end 12b. The probe body 12 has an elongated, substantially cylindrical stem 14 defining a longitudinally extending bore 16 formed therein. A hole 17, the purpose for which is described below, may be formed in the stem 14. The second end of the probe body 12 defines a cup 18. Longitudinally extending notches 20 are formed in a wall of the cup 18. The probe body 12 may be formed from brass. Alternatively, the probe body 12 may be formed from other metals, such as copper, metal alloys, and other conductive material.

In the illustrated embodiment, the stem 14 has an outside diameter of about 0.625 inches. Alternatively, the stem 14 may have any other desired diameter, such as a diameter within the range of about 0.50 inches to about 0.75 inches. In the illustrated embodiment, the cup 18 has an outside diameter of about 1.250 inches. Alternatively, the cup 18 may have any other desired diameter, such as a diameter within the range of about 1.125 inches to about 1.375 inches. The probe body 12 may have a length of about 10.715 inches. Alternatively, the probe body 12 may have any other desired length that may be determined based on the application in which the MEC probe 10 will be used.

A wiring assembly 22 is mounted within the bore 16 of the stem 14. The wiring assembly 22 includes wiring cable 24, such as a flat ribbon cable. A first end of the wiring assembly 22 includes a connector 26 disposed within the cup 18 and configured for connection to a MEC printed circuit board (PCB) assembly 32, described below. A cable shield 28 surrounds the wiring cable 24, and a connector 30 is attached to a second end of the wiring assembly 22. The connector 30 is configured for attachment within the bore 16 at the open second end 12b of the probe body 12, such as with a threaded connection, and further configured for attachment to a source of electrical power (not shown). The connector may be further sealed within the bore 16 with an adhesive, such as Torr Seal® epoxy resin.

Figure 2A:
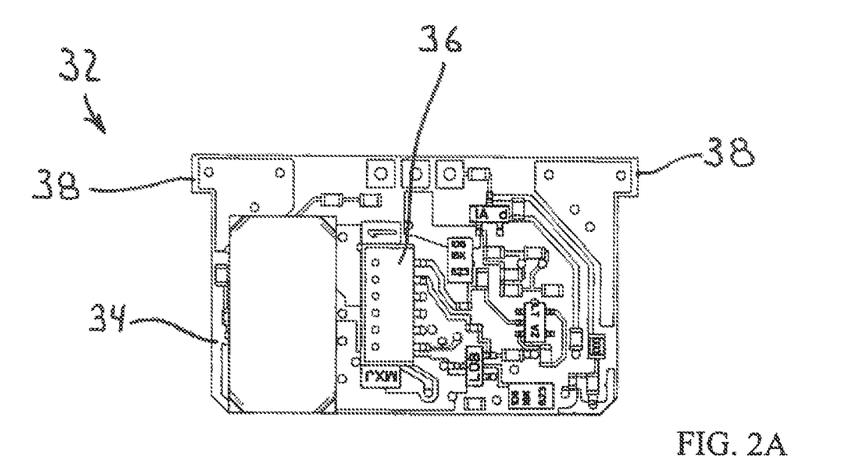
FIG. 2A is a plan view of the MEC printed circuit board (PCB) assembly illustrated in FIG. 1.
Figure 2B:
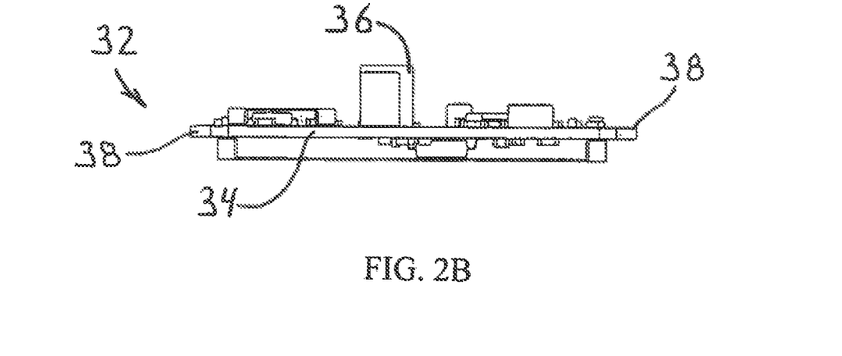
FIG. 2B is a side view of the MEC PCB assembly illustrated in FIGS. 1 and 2A.

The MEC PCB assembly 32, also shown in FIGS. 2A and 2B, includes a conventional circuit board 34 configured to have mounted thereon electronic components, such as capacitors, resistors, voltage regulators, and the like. A connector 36, such as a six pin connector (see FIGS. 1, 2A, and 6D), is mounted to the circuit board 34 and is configured for attachment to the connector 26 of the wiring assembly 22. The circuit board 34 is substantially rectangular in shape, defines a large ground plane, and includes outwardly extending tabs or flanges 38 configured for mounting within the notches 20.

A conventional eddy current probe typically includes: (1) one or more coils which provide an electro-magnetic field that induces eddy currents in a surface, (2) an oscillator configured to drive the one or more coils with a sine wave at a desired frequency that is determined by the application, (3) a sensing circuit to sense changes in the coupling between the one or more coils and the induced eddy currents in the surface, and (4) an electronic interface that processes the output of the sensed circuit and transmits the output information to a processor.

The MEC probe 10 described herein improves upon conventional eddy current probes, provides a compact, inexpensive package, and includes a coil board assembly 40, shown in FIGS. 1 and 3 through 5. The coil board assembly 40 includes a substantially circular coil board 42, formed from one or more layers 42A, 42B of conventional circuit board material, such as FR4. Alternatively, the coil board 42 may be formed from any glass-reinforced epoxy laminate or other desired material. The coil board 42 has a size and shape corresponding to the opening of the cup 18, and is configured to be attached within the cup 18 at the open first end 12a of the probe body 12, and is also configured for electrical connection to the MEC PCB assembly 32. Further, electric grounds (not shown) on the MEC PCB assembly 32 and on the coil board assembly 40 may be soldered to the wall of the cup 18 to minimize stray capacitance. These solder joints also serve as connection joints to attach the MEC PCB assembly 32 and the coil board assembly 40 to the cup 18.

Figures 3, 5:
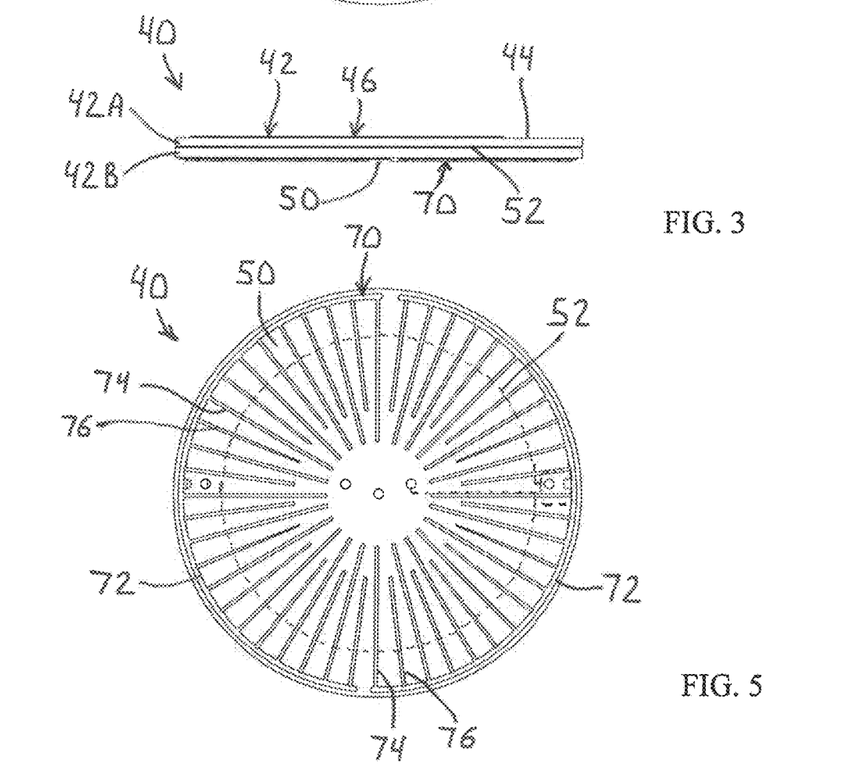
FIG. 3 is an enlarged side view of the coil board assembly illustrated in FIG. 1.
FIG. 5 is a plan view of an outside surface of the coil board assembly illustrated in FIG. 1 showing the sensor coil.

In the illustrated embodiment, the coil board 42 has an outside diameter of about 1.250 inches. Alternatively, the coil board 42 may have any other desired diameter, such as a diameter within the range of about 1.125 inches to about 1.375 inches.

Figure 4:
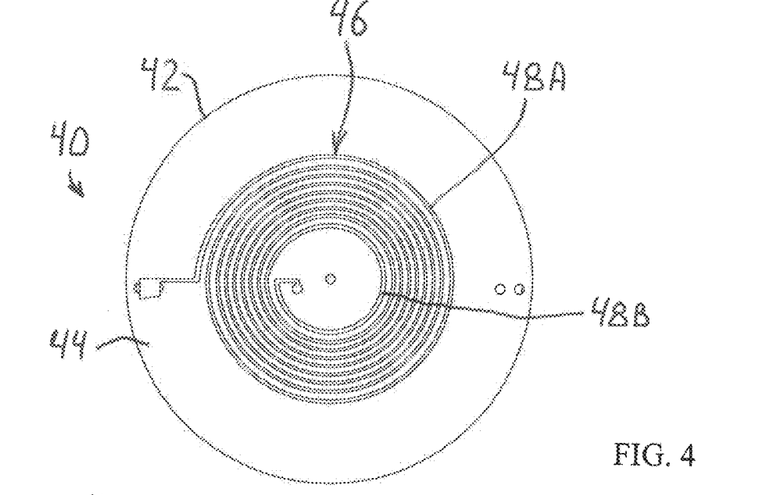
FIG. 4 is a plan view of an inside surface of the coil board assembly illustrated in FIG. 1 showing the transmitter coil.

A first or inside surface 44 of the coil board 42 includes a transmitter coil 46 formed thereon by any desired method, such as conventional PCB manufacturing methods. The transmitter coil 46 includes nine loops and the terminal ends thereof are attached to the coil board 42 such as with solder. Alternatively, the transmitter coil 46 may have other desired numbers of loops, including less than nine loops and more than nine loops.

An outer loop 48A of the transmitter coil 46 may have a diameter of about 0.75 inches, and an inner loop 48B of the transmitter coil 46 may have a diameter of about 0.43 inches. Alternatively, the outer loop 48A and the inner loop 48B may have any other desired diameters that may be determined based on the application in which the MEC probe 10 will be used and the desired transmitter frequency.

A second or outside surface 50 of the coil board 42 includes a Faraday shield 70 formed thereon. Like the transmitter coil 46, the Faraday shield 70 may be formed on the surface 50 by any desired method, such as conventional PCB manufacturing methods. The Faraday shield 70 includes two substantially semicircular outer loop portions 72. Each outer loop portion 72 includes a plurality of radially inwardly extending first spokes 74 and second spokes 76. In the illustrated embodiment, the first spokes 74 have a first length longer than a second length of the second spokes 76. The spokes are configured in an alternating arrangement such that every other spoke is a first spoke 74 separated by a second spoke 76.

A sensor coil 52 may be formed on an inside surface of either of the layers 42A and 42B of the coil board 42 before the layers 42A and 42B are bonded together. Like the transmitter coil 46 and the Faraday shield 70, the sensor coil 52 may be formed on the inside surface of either of the layers 42A and 42B by any desired method, such as conventional PCB manufacturing methods. The sensor coil 52 includes a single loop having a diameter of about 1.0 inch and the terminal ends thereof are attached to the coil board 42 such as with solder. Alternatively, the sensor coil 52 may have other diameters determined by the size of the coil board 42 and the size of the transmitter coil 46.

The transmitter coil 46, the sensor coil 52, and the Faraday shield 70, may be formed from copper. Alternatively, the transmitter coil 46, the sensor coil 52, and the Faraday shield 70 may be formed from other desired conductive material such as silver.

Significantly, conventional eddy current probes typically do not include a separate sensor coil, but instead monitor an output of the oscillator tank circuit directly. Advantageously, the sensor coil 52 functions as a very high Q filter of the fields induced in the surface of the low conductivity material of the target, and therefore provides sine waves with small harmonics that reduces error in subsequent signal processing.

Figure 6A:
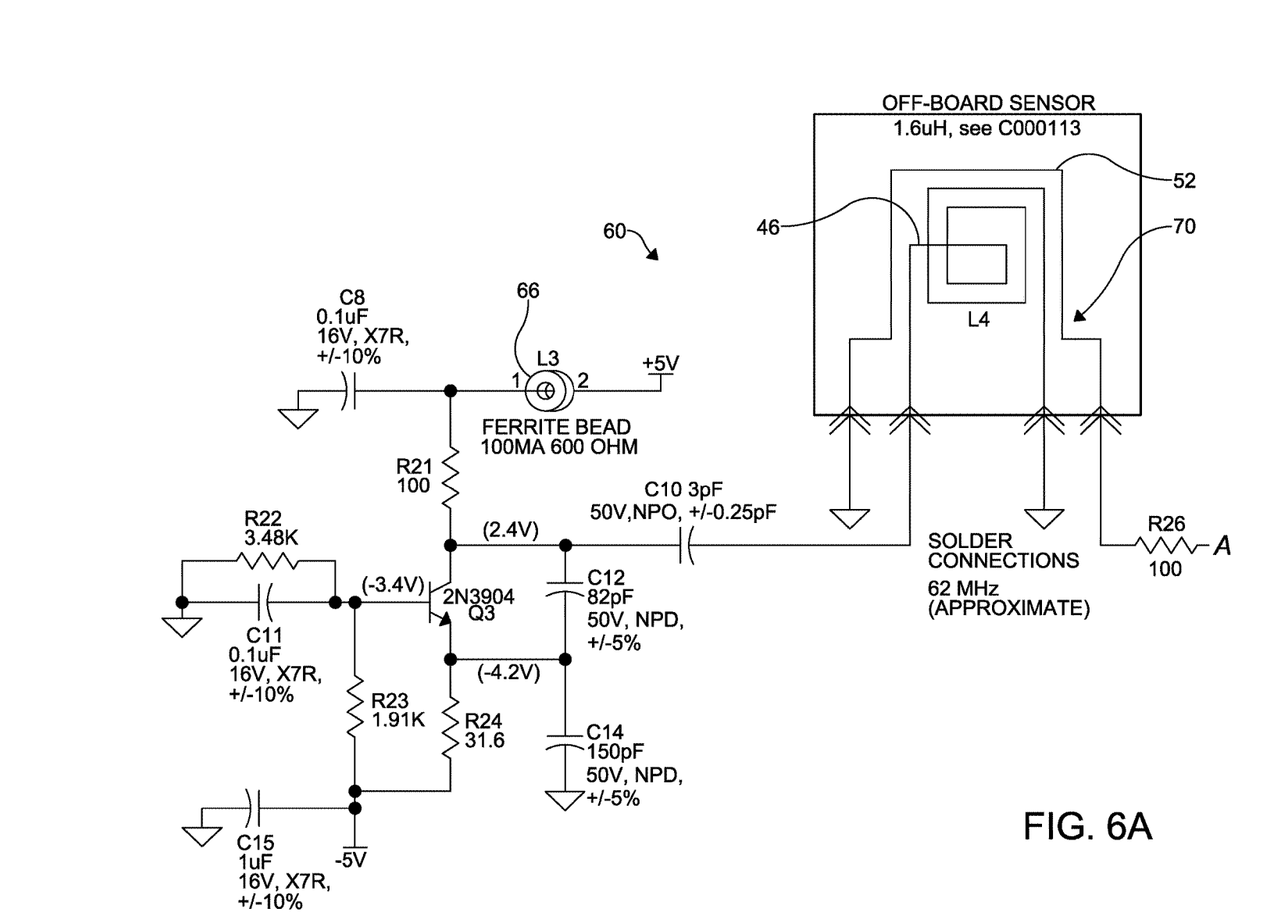
FIGS. 6A, 6B, 6C, and 6D are a circuit diagram for the MEC probe illustrated in FIG. 1.
Figure 6B:
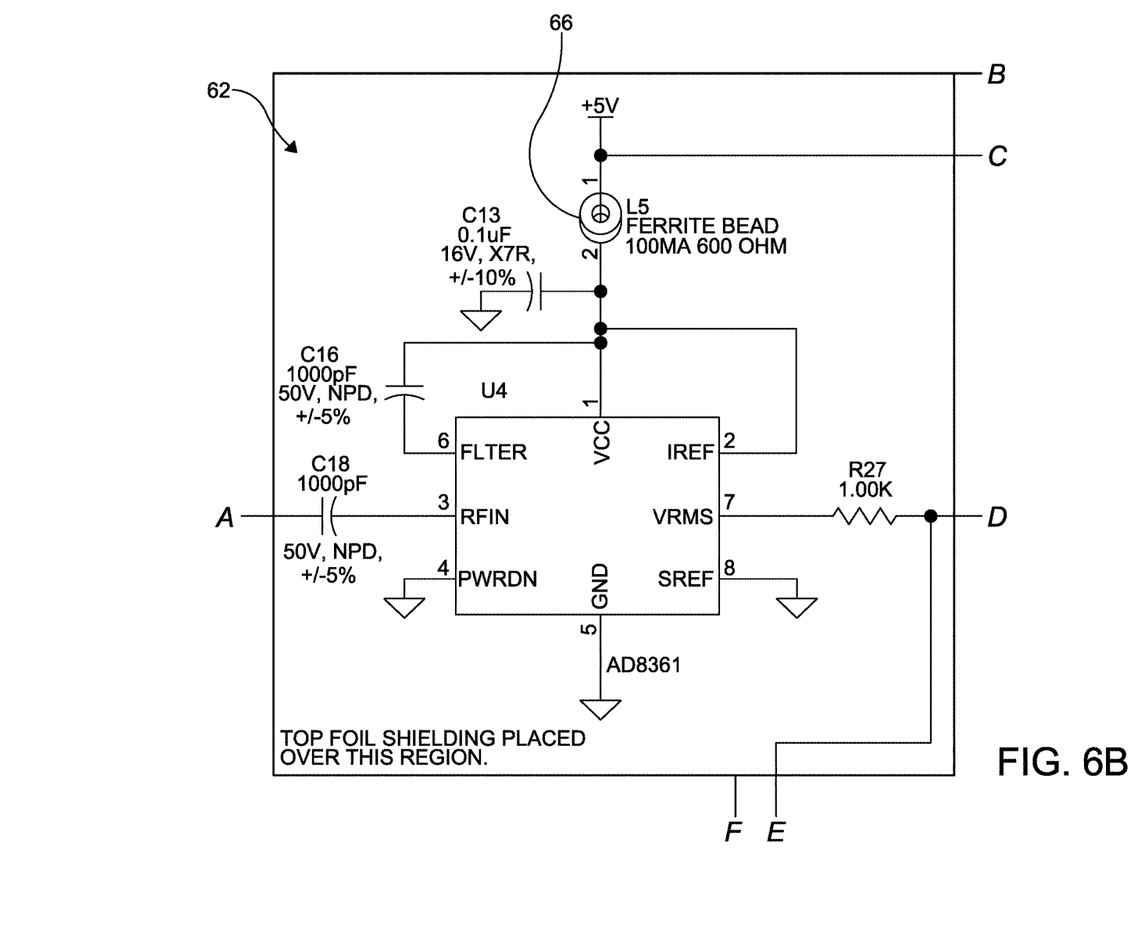
Figure 6C:
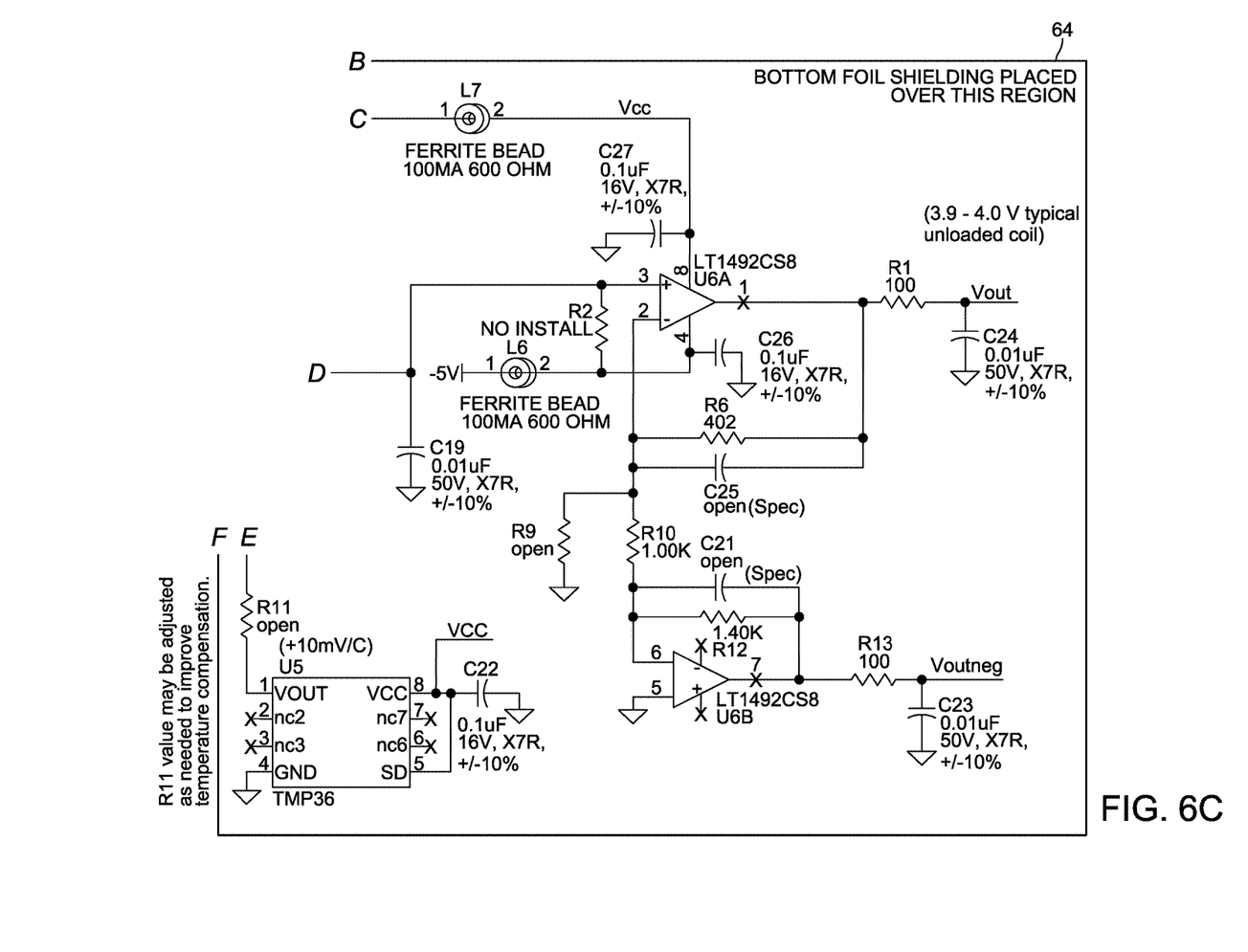
Figure 6D:
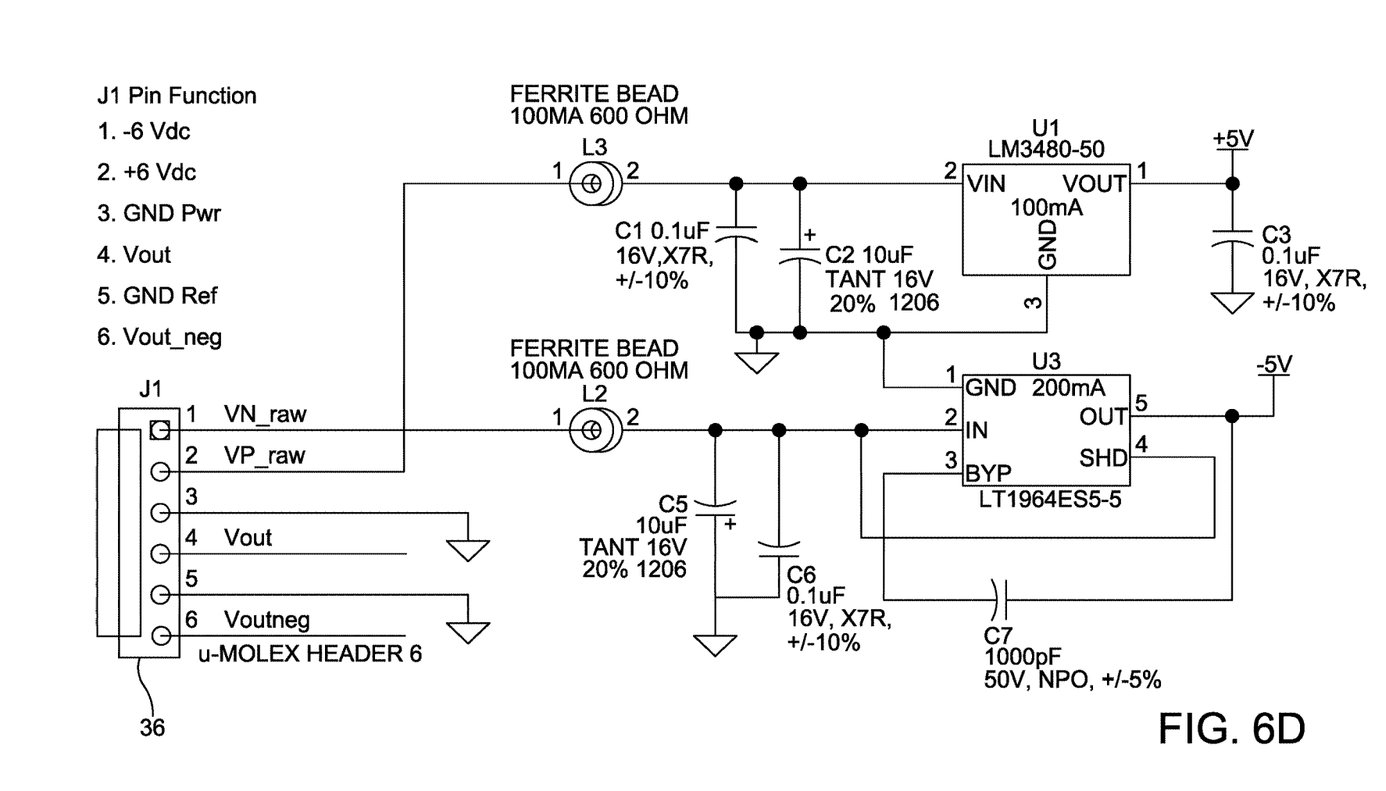

The MEC PCB assembly 32 includes an oscillator circuit 60 that drives the transmitter coil 46 (see the circuit diagram of the MEC probe 10 shown in FIGS. 6A-6D). It has been discovered that it is possible to induce surface eddy currents in low conductivity materials, such as graphite by using a high frequency radio frequency (RF) sine wave. The magnitude power dissipation of the surface eddy currents is proportional to the volume resistivity of the low conductivity material and a distance between the surface and the transmitter coil 46. As shown in FIG. 6A, a sine wave having a frequency of about 62 MHz may be used.

The oscillator circuit 60 used to generate the about 62 MHz sine wave may be a conventional Clapp oscillator circuit having a single bipolar transistor and passive biasing. In this arrangement, the oscillation frequency may be largely determined by a tank circuit that includes the transmitter coil (L4 in FIG. 6A) and a capacitor C10. The target material, i.e., the graphite or other low conductivity material, may resistively load the tank circuit resulting in decreasing oscillation amplitude as a distance to the target decreases.

The MEC probe 10 further includes improved interface electronics. As shown generally at 62 in FIG. 6B, a signal from the sensor coil (L4 in FIG. 6A) may drive U4, an analog device, such as an AD8361, and a true root mean square (RMS) high frequency integrated circuit. The output of U4 is a DC voltage proportional to the RMS value of the RF signal input. Additional low-pass filtering may be provided by R27 and c19 to limit the output bandwidth to about 15.9 kHz. The output may be buffered by U6, such as a Linear Technology LT1492 operational amplifier (op-amp), and provides a differential output.

The MEC probe 10 further includes improved interface electronics. As shown generally at 62 in FIG. 6, a signal from the sensor coil (L4 in FIG. 6) may drive U4, an analog device, such as an AD836 1, and a true root mean square (RMS) high frequency integrated circuit. The output of U4 is a DC voltage proportional to the RMS value of the RF signal input. Additional low-pass filtering may be provided by R27 and C 19 to limit the output bandwidth to about 15.9 kHz. The output may be buffered by U6, such as a Linear Technology LT1492 operational amplifier (op-amp), and provides a differential output.

The improved interface electronics also includes supporting voltage supplies and noise minimization components. The input DC supply voltages are heavily filtered, and may be regulated on the MEC PCB assembly 32 by low drop-out voltage regulator chips U1 and U3, such as a National Semiconductor LM3480-5.0 and a Linear Technology LT1964ES5-5, respectively. The LM3480 is a positive regulator that requires a minimum of 0.8 V headroom to maintain regulation. The LT1964 is a negative regulator that requires less than 0.3 V headroom to maintain regulation. In the MEC probe 10 described herein, an optimal supply voltage has been determined to be 6.2 V in order to allow for voltage drop along the cable and still provide a comfortable margin of headroom at the MEC PCB assembly 32.

The packaging and relative positions of the components of the MEC probe 10 (see FIG. 1) have been shown to be key to the successful operation of the MEC probe 10. Because the frequency of the transmitter coil 46 is above about 50 MHz (in the embodiment described above, the transmitter coil 46 operates at about 62 MHz), the transmitter coil 46, the sensor coil 52 and the various electronic components mounted on the MEC PCB assembly 32 must be positioned in close proximity to each other to minimize undesirable stray capacitance and to reduce undesirable noise.

As shown in FIG. 1, the MEC PCB assembly 32 is oriented substantially orthogonally to the transmitter coil 46 and the sensor coil 52 formed on the coil board 42. This orthogonal orientation reduces unwanted coupling of electro-magnetic fields from the transmitter coil 46 to the various electronic components of the MEC PCB assembly 32. Alternatively, the MEC PCB assembly 32 may be oriented at other angles relative to the transmitter coil 46 and the sensor coil 52 formed on the coil board 42, such as within the range of about 90 degrees+/−about 10 degrees. Additionally, the MEC PCB assembly 32 may be oriented at other desired angles relative to the transmitter coil 46 and the sensor coil 52 formed on the coil board 42. Additionally, the multi-loop transmitter coil 46 and the single-loop sensor coil 52 on the respective inside surface 44 and outside surface 50 of the coil board 42 reduce pick-up signal distortions and increases accuracy in the RMS signal processing step.

As shown, the MEC PCB assembly 32 is electrically connected to the inside surface 44 of the coil board 42. Contacts (not shown) on the transmitter coil 46 may be electrically connected to contacts (not shown) on the MEC PCB assembly 32, such as with solder, using very short leads, such as 1/10 of a wavelength or less.

To further assist in noise reduction, a copper shield, schematically illustrated in FIGS. 6B and 6C, may be placed over any desired components of the MEC PCB assembly 32 that are determined to be RF sensitive. In addition to the low drop-out voltage regulator chips U1 and U3, ferrite beads 66 (see FIGS. 6A-6D) may be provided on any electrical line or cable to isolate the power sources.

To further assist in noise reduction, a copper shield, schematically illustrated in FIG. 6, may be place over any desired components of the MEC PCB assembly 32 that are determined to be RF sensitive. In addition to the low drop-out voltage regulator chips U1 and U3, ferrite beads 66 (see FIG. 6) may be provided on any electrical line or cable to isolate the power sources.

In applications wherein the MEC probe 10 is mounted for operation in a vacuum, the hole 17 in the stem 14 allows pressure to equalize across the transmitter coil 46.

Additionally, the single loop sensor coil and multiple loop transmitter coil formed on the respective outside and inside surfaces of the coil board assembly 40 reduce pick-up signal distortion and increase accuracy in the RMS conversion processing step (see 62 in FIG. 6B) in a compact and inexpensive package.

Further, the features of the improved MEC probe 10, including: the ability to successfully operate at RF frequencies above about 50 MHz, the MEC PCB assembly 32 being oriented orthogonally to the transmitter coil 46 and the sensor coil 52 formed on the coil board assembly 40, the sensor coil 52 being formed on an outside surface 50 of the coil board assembly 40, the short lead connections between the transmitter coil 46 and the MEC PCB assembly 32, the most electronically sensitive components on the MEC PCB assembly 32 being positioned a maximum distance from the center of the transmitter coil 46, the ferrite beads on the power lines, the isolated power sources, the copper shields on RF sensitive components, and the large ground planes on the MEC PCB assembly 32.

It is desirable in certain applications to use two or more MEC probes 10 is a probe system to measure the distance to multiple locations on the surface of the object. In such applications, and particularly when the object and the MEC probes 10 are arranged in a closed reflective space defining a cavity resonator. In addition to the electro-magnetic fields from the transmitter coil 46, the oscillator circuit 60 also emits a propagating transverse electro-magnetic (TEM) field. The propagating TEM fields from two or more MEC probes 10 may couple within the reflective space and cause undesirable signal enhancement or signal cancellation from the transmitter coils 46 of adjacent and/or closely spaced MEC probes 10. This may result in non-stationary measurement errors in all of the MEC probes 10 in the reflective space.

Advantageously, the Faraday shield 70 isolates the propagating TEM fields from the two or more MEC probes 10.

The design of the coil board assembly 40, including the Faraday shield 70, and its substantially orthogonal orientation relative to the MEC PCB assembly 32 is ensures that unwanted coupling of electro-magnetic fields from the transmitter coil 46 to the various electronic components of the MEC PCB assembly 32 is significantly reduced.

Additionally, the Faraday shield 70 creates a short circuit to the propagating transverse electro-magnetic (TEM) field that defines a reflective boundary to the propagating transverse electro-magnetic (TEM) field from an adjacent MEC probe 10 and results in a reduction in the cross coupling between MEC probes 10 in the reflective space of about 20 dB. Advantageously, the Faraday Shield 70 reduces noise and cross-talk between closely spaced MEC probes 10 that are used to measure distances between the MEC probes 10 and the surface of the object being measured. Thus, the addition of the Faraday shield 70 to the coil board assembly 40 acts to preserve the accuracy of the distance measurement between the MEC probes 10 and the surface of the object being measured.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A modified eddy current (MEC) probe comprising:
   a probe body having a bore formed therein;
   a printed circuit board (PCB) assembly including a circuit board defining a plane and having a plurality of electronic components mounted thereon, the PCB assembly configured for mounting within the bore of the probe body; and
   a coil board assembly electrically connected to the PCB assembly, the coil board assembly defining a plane and comprising:
   a first coil board layer;
   a second coil board layer bonded to the first coil board layer;
   a transmitter coil formed on an outside surface of the first coil board layer;
   a Faraday shield formed on an outside surface of the second coil board layer; and
   a sensor coil formed on one of an inside surface of the first coil board layer and the second coil board layer, such that the sensor coil is positioned between the first coil board layer and the second coil board layer;
   wherein the plane of the coil board assembly is arranged orthogonally to the plane of the circuit board.

2. The MEC probe according to claim 1, wherein the Faraday shield includes two semi-circular outer loop portions, each outer loop portion having a plurality of radially inwardly extending first spokes and radially inwardly extending second spokes, and wherein the first spokes are longer than the second spokes.

3. The MEC probe according to claim 2, wherein the first and second spokes are configured in an alternating arrangement such that every other spoke is a first spoke separated by a second spoke.

4. The MEC probe according to claim 3, wherein the coil board assembly is mounted within the bore of a distal end of the probe body.

5. The MEC probe according to claim 3, wherein the transmitter coil operates at a frequency greater than about 10 MHz.

6. The MEC probe according to claim 3, wherein the transmitter coil operates at a frequency greater than about 50 MHz.

7. The MEC probe according to claim 3, wherein the transmitter coil operates at a frequency of about 62 MHz.

8. The MEC probe according to claim 3, wherein the transmitter coil generates an electro-magnetic signal configured to measure a distance to a surface of an object formed from a material having low conductivity.

9. The MEC probe according to claim 3, wherein the transmitter coil generates an electro-magnetic signal configured to measure a distance to a surface of an object formed from graphite.

10. The MEC probe according to claim 3, wherein the transmitter coil operates at a frequency greater than about 10 MHz and measures a distance to the surface of the object formed from a material having low conductivity with less than about 0.1 mil sensitivity over a range of about 400 mils.

11. The MEC probe according to claim 3, wherein the transmitter coil operates at a frequency greater than about 10 MHz and measures a distance to the surface of the object formed from graphite with less than about 0.1 mil sensitivity over a range of about 400 mils.

12. The MEC probe according to claim 3, wherein the transmitter coil is a multi-loop coil.

13. The MEC probe according to claim 3, wherein the transmitter coil is a nine-loop coil.

14. The MEC probe according to claim 3, wherein the sensor coil is a single-loop coil.

15. The MEC probe according to claim 13, wherein the sensor coil is a single-loop coil.

16. The MEC probe according to claim 3, wherein contacts on the transmitter coil are electrically connected to contacts on the PCB assembly with leads of $\frac{1}{10}$ of a wavelength or less.

17. The MEC probe according to claim 3, further including ferrite beads on at least one electrical line, the ferrite beads configured to isolate power sources within the MEC probe.

18. A modified eddy current (MEC) probe system comprising:
   a plurality of MEC probes configured to cooperate with each other, each MEC probe including:
   a probe body having a bore formed therein;

a printed circuit board (PCB) assembly including a circuit board defining a plane and having a plurality of electronic components mounted thereon, the PCB assembly configured for mounting within the bore of the probe body; and a coil board assembly electrically connected to the PCB assembly, the coil board assembly defining a plane and including:
- a first coil board layer;
- a second coil board layer bonded to the first coil board layer;
- a transmitter coil formed on an outside surface of the first coil board layer,
- a Faraday shield formed on an outside surface of the second coil board layer; and
- a sensor coil formed on one of an inside surface of the first coil board layer and the second coil board layer, such that the sensor coil is positioned between the first coil board layer and the second coil board layer, wherein the plane of the coil board assembly is arranged orthogonally to the plane of the circuit board;

wherein the Faraday shields are configured to isolate a propagating transverse electro-magnetic (TEM) field emitted by each MEC probe and to one of prevent and reduce coupling of electro-magnetic fields from the transmitter coil to the plurality of electronic components mounted on the PCB assembly.

19. The MEC probe system according to claim 18, wherein the Faraday shield in each MEC probe is further configured to create a short circuit to the propagating TEM field that defines a reflective boundary to the propagating TEM field from an adjacent MEC probe.

20. The MEC probe system according to claim 19, wherein the short circuit to the propagating TEM field that defines a reflective boundary to the propagating TEM field from an adjacent MEC probe also causes a reduction in cross coupling between MEC probes in the reflective space of about 20 dB.

* * * * *